(12) United States Patent
Sabir et al.

(10) Patent No.: US 9,414,856 B2
(45) Date of Patent: Aug. 16, 2016

(54) DEVICES FOR GENERATING AND TRANSFERRING MICROGRAFTS AND METHODS OF USE THEREOF

(71) Applicant: MoMelan Technologies, Inc., Cambridge, MA (US)

(72) Inventors: Sameer Sabir, Cambridge, MA (US); Brian Newkirk, London (GB); Andrew Ziegler, Arlington, MA (US); Denis Labombard, Georgetown, MA (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 14/019,292

(22) Filed: Sep. 5, 2013

(65) Prior Publication Data
US 2014/0046344 A1    Feb. 13, 2014

Related U.S. Application Data

(62) Division of application No. 13/014,737, filed on Jan. 27, 2011, now abandoned.

(51) Int. Cl.
*A61B 17/00* (2006.01)
*A61B 17/322* (2006.01)
*A61B 17/30* (2006.01)

(52) U.S. Cl.
CPC ......... *A61B 17/322* (2013.01); *A61B 2017/306* (2013.01)

(58) Field of Classification Search
CPC ..................... A61B 17/322; A61B 2017/306
USPC ......... 606/132, 167, 168, 171–173, 180–186; 83/684, 563, 701, 588, 618, 648
See application file for complete search history.

(56) References Cited

U.S. PATENT DOCUMENTS

| | | | |
|---|---|---|---|
| 4,666,447 A | 5/1987 | Smith | |
| 5,015,584 A | 5/1991 | Brysk | |
| 5,476,478 A | 12/1995 | Jackson | |
| 5,545,222 A | 8/1996 | Bonutti | |
| 5,686,303 A | 11/1997 | Korman | |
| 5,759,193 A | 6/1998 | Burbank | |
| 5,888,219 A * | 3/1999 | Bonutti | .................. 128/898 |
| 5,914,264 A | 6/1999 | Korman | |
| 6,248,114 B1 | 6/2001 | Ysebaert | |

(Continued)

FOREIGN PATENT DOCUMENTS

| | | |
|---|---|---|
| WO | 9528886 | 11/1995 |
| WO | WO2010036788 | * 4/2010 |

OTHER PUBLICATIONS

Related U.S. Appl. No. 13/120,799, Office Action dated Dec. 18, 2014.

(Continued)

*Primary Examiner* — Ryan J Severson
*Assistant Examiner* — Anh Dang
(74) *Attorney, Agent, or Firm* — Tom Engellenner; Reza Mollaaghababa; Pepper Hamilton, LLP

(57) ABSTRACT

The invention generally relates to devices for generating and transferring micrografts and methods of use thereof. In certain embodiments, devices of the invention include a housing having an open configuration and a closed configuration, a micrograft generating station, and a micrograft transferring station.

20 Claims, 10 Drawing Sheets

(56) References Cited

U.S. PATENT DOCUMENTS

| | | | |
|---|---|---|---|
| 6,860,904 B2 | 3/2005 | Bonutti | |
| 7,078,582 B2 | 7/2006 | Stebbings | |
| 7,208,006 B2 | 4/2007 | Fleischmann | |
| 7,244,444 B2 | 7/2007 | Bates | |
| 7,625,384 B2 | 12/2009 | Eriksson | |
| 7,666,134 B2 | 2/2010 | Eriksson | |
| 7,708,746 B2 | 5/2010 | Eriksson | |
| 7,727,760 B2 * | 6/2010 | Guu et al. | 435/309.1 |
| 2004/0172045 A1 | 9/2004 | Eriksson | |
| 2004/0225309 A1 | 11/2004 | Eriksson | |
| 2004/0230215 A1 | 11/2004 | Eriksson | |
| 2004/0237744 A1 | 12/2004 | Lin | |
| 2006/0141616 A1 | 6/2006 | Guu | |
| 2006/0258956 A1 | 11/2006 | Haberstich et al. | |
| 2006/0271070 A1 | 11/2006 | Eriksson | |
| 2007/0255168 A1 | 11/2007 | Hibner et al. | |
| 2010/0042127 A1 | 2/2010 | Eriksson | |
| 2010/0145360 A1 | 6/2010 | Eriksson | |

OTHER PUBLICATIONS

Awad, Chinese Cupping: A Simple Method to Obtain Epithelial Grafts for the Management of Resistant Localized Vitiligo, American Society of Dermatologic Surgery, Inc., Dermatol Surg, (2008), 34(9):1186-1193.

Kreis et al., Expansion techniques for skin grafts: comparison between mesh and Meek Island (sandwich-) grafts, Burns, (1994), 20(1):S39-S42.

Lari et al., Expansion technique for skins grafts (Meek technique) in the treatment of severely burned patients, Burns, (2001), 27:61-66.

Mulekar et al., Treatment of Vitiligo on Difficult-to-Treat Sites Using Autologous Noncultured Cellular Grafting, Dermatol Surg., (2009), 25(1):66-71.

Meek et al., Successful Microdermagrafting Using the Meek-Wall Microdermatome, Am J Surg, (1958), 96(4):557-558.

* cited by examiner

DEVICES FOR GENERATING AND TRANSFERRING MICROGRAFTS AND METHODS OF USE THEREOF

REFERENCE TO RELATED APPLICATION

This application is a division of U.S. application Ser. No. 13/014,737 filed Jan. 27, 2011, entitled "Devices For Generating And Transferring Micrografts And Methods Of Use Thereof," the contents of which is incorporated by reference in its entirety.

FIELD OF THE INVENTION

The invention generally relates to devices for generating and transferring micrografts and methods of use thereof.

BACKGROUND

Skin is the largest organ of the human body, representing approximately 16% of a person's total body weight. Because it interfaces with the environment, skin has an important function in body defense, acting as an anatomical barrier from pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation (e.g., vitiligo).

Skin grafts are often used to repair such skin damage. Skin grafting is a surgical procedure in which a section of skin is removed from one area of a person's body (autograft), removed from another human source (allograft), or removed from another animal (xenograft), and transplanted to a recipient site of a patient, such as a wound site. As with any surgical procedure, skin grafting includes certain risks. Complications may include: graft failure; rejection of the skin graft; infections at donor or recipient sites; or autograft donor sites oozing fluid and blood as they heal. Certain of these complications (e.g., graft failure and rejection of the skin graft) may be mitigated by using an autograft instead of an allograft or a xenograft.

A problem encountered when using an autograft is that skin is taken from another area of a person's body to produce the graft, resulting in trauma and wound generation at the donor site. Generally, the size of the graft matches the size of the recipient site, and thus a large recipient site requires removal of a large section of skin from a donor site. As the size of the section of skin removed from the donor site increases, so does the probability that the donor site will not heal properly, requiring additional treatment and intervention. Additionally, as the size of the section of skin removed from the donor site increases, so does the possibility of infection. There is also increased healing time associated with removal of larger sections of skin because a larger wound is produced.

To address those problems, techniques have been developed that allow for expansion of a skin graft so that a harvested graft can treat a recipient site that is larger than a donor site. Such methods involve cutting a skin graft into many smaller micrografts, transferring the micrografts onto a substrate, expanding the micrografts on the substrate, and applying the expanded substrate having the expanded micrografts to a recipient site. Producing micrografts and transferring micrografts is typically accomplished using two devices, one device to cut the skin graft into the many smaller micrografts, and a second device to transfer the micrografts from the cutting surface to a substrate for expansion. The need for two devices slows the grafting process and increases the risk of graft failure. Further, the need for separate devices has prevented development of an automated system for producing a skin graft.

SUMMARY

The present invention provides a micrograft generating device integrated with a micrograft transferring device. The invention thus provides a single device that can generate a plurality of micrografts and transfer the micrografts to a substrate.

In certain embodiments, devices of the invention include a housing having an open configuration and a closed configuration, a micrograft generating station, and a micrograft transferring station. The housing may include a bottom portion hingedly connected to a top portion. Generally, the top portion of the housing is movable in a vertical direction.

In certain embodiments, the micrograft generating station includes a first member connected to the top portion of the housing, and a second member connected to the bottom portion of the housing, in which the first member is aligned with the second member. In certain embodiments, the micrograft transferring station includes a transfer pusher including a plurality of prongs, in which the pusher is connected to the top portion of the housing, and a transfer stage connected to the bottom portion of the housing, in which the pusher and the stage are aligned with each other. The transfer stage may be made of any material that is softer than that of the transfer pusher. In certain embodiments, the transfer stage is composed of a compressible material. In other embodiments, the transfer stage includes a spring loaded base. The spring loaded base may further include a ball to focus the force on the center of the stage.

The housing may further include a cartridge receiving portion, in which the cartridge receiving portion is located between the top portion and the bottom portion of the housing. The cartridge receiving portion may include a first slot and a second slot, in which the first slot is aligned with the micrograft generating station and the second slot is aligned with the micrograft transferring station. Alternatively, the cartridge receiving portion may include a single slot and components of the micrograft generating station and the micrograft transferring station are removable from the top and bottom portions of the housing, thereby providing for the micrograft generating station and the micrograft transferring station to be located at a same place in the device.

Devices of the invention may further include a cartridge that is compatible with the first slot and the second slot of the cartridge receiving portion. Further, the cartridge may be removable from the first and second slots of the cartridge receiving portion. The cartridge is configured to hold a skin graft. In certain embodiments, the cartridge includes a frame having a hollow inner portion, a removable first plate including a mesh grid, and a removable second plate including a mesh grid, in which, in an assembled configuration, the grid of the first plate and the grid of the second plate are aligned with the hollow portion of the frame, and the grid of the first plate is aligned with the grid of the second plate. In certain embodiments, holes in the grids of the first and second plates are generally larger than the prongs of the transfer pusher.

Another aspect of the invention provides methods for generating and transferring micrografts, including providing a device having a housing having an open configuration and a closed configuration, a micrograft generating station, and a micrograft transferring station, inserting a skin graft into the device, engaging the micrograft generating station, thereby generating a plurality of micrografts, and engaging the micrograft transferring station, thereby transferring the plurality of micrografts to a substrate.

In certain embodiments, inserting includes obtaining a cartridge having a frame including a hollow inner portion, a removable first plate having a mesh grid, and a removable second plate having a mesh grid, in which in an assembled configuration, the grid of the first plate and the grid of the second plate are aligned with the hollow portion of the frame, and the grid of the first plate is aligned with the grid of the second plate, and inserting the skin graft between the first and second plates such that the graft is aligned with the grids in the first and second plates.

In certain embodiments, engaging the micrograft generating station includes inserting the cartridge into the micrograft generating station of the device while the housing is in the open configuration, and transforming the housing from the open configuration to the closed configuration, thereby generating a plurality of micrografts. In certain embodiments, engaging the micrograft transferring station includes inserting the cartridge into the micrograft transferring station of the device while the housing is in the open configuration, inserting a substrate below the cartridge, and transforming the housing from the open configuration to the closed configuration, thereby transferring the plurality of micrografts to the substrate. The substrate may be any biocompatible material. An exemplary substrate is a medical dressing.

Methods of the invention are used with any type of skin graft, such as an epidermal skin graft, a split thickness graft, or a full thickness graft. In particular embodiments, methods of the invention are used with skin grafts including only or substantially only the epidermal layer of skin. Methods of the invention can be used with autografts, allografts, or xenografts. In preferred embodiments, the grafts are autografts.

Methods of the invention may also include harvesting the skin graft. Harvesting of skin grafts can occur by any method known in the art. In certain embodiments, harvesting involves raising a blister, and cutting the blister to obtain the skin graft. In certain embodiments, raising involves contacting a device having a hole to skin, and applying heat and/or vacuum pressure, thereby raising the blister.

Methods of the invention may further include expanding the micrografts, and applying the expanded grafts to a patient recipient site. Methods of the invention are used to prepare skin grafts for any recipient site of damaged skin. Exemplary types of skin damage include burns (e.g., thermal or chemical), infections, wounds, or depigmentation. In particular embodiments, the recipient site is an area of depigmented skin that has been prepared to receive a skin graft.

BRIEF DESCRIPTION OF THE DRAWINGS

FIG. 4A shows an exploded view of the cartridge. FIG. 4B shows a view of a fully assembled cartridge.

DETAILED DESCRIPTION

Figure 1:
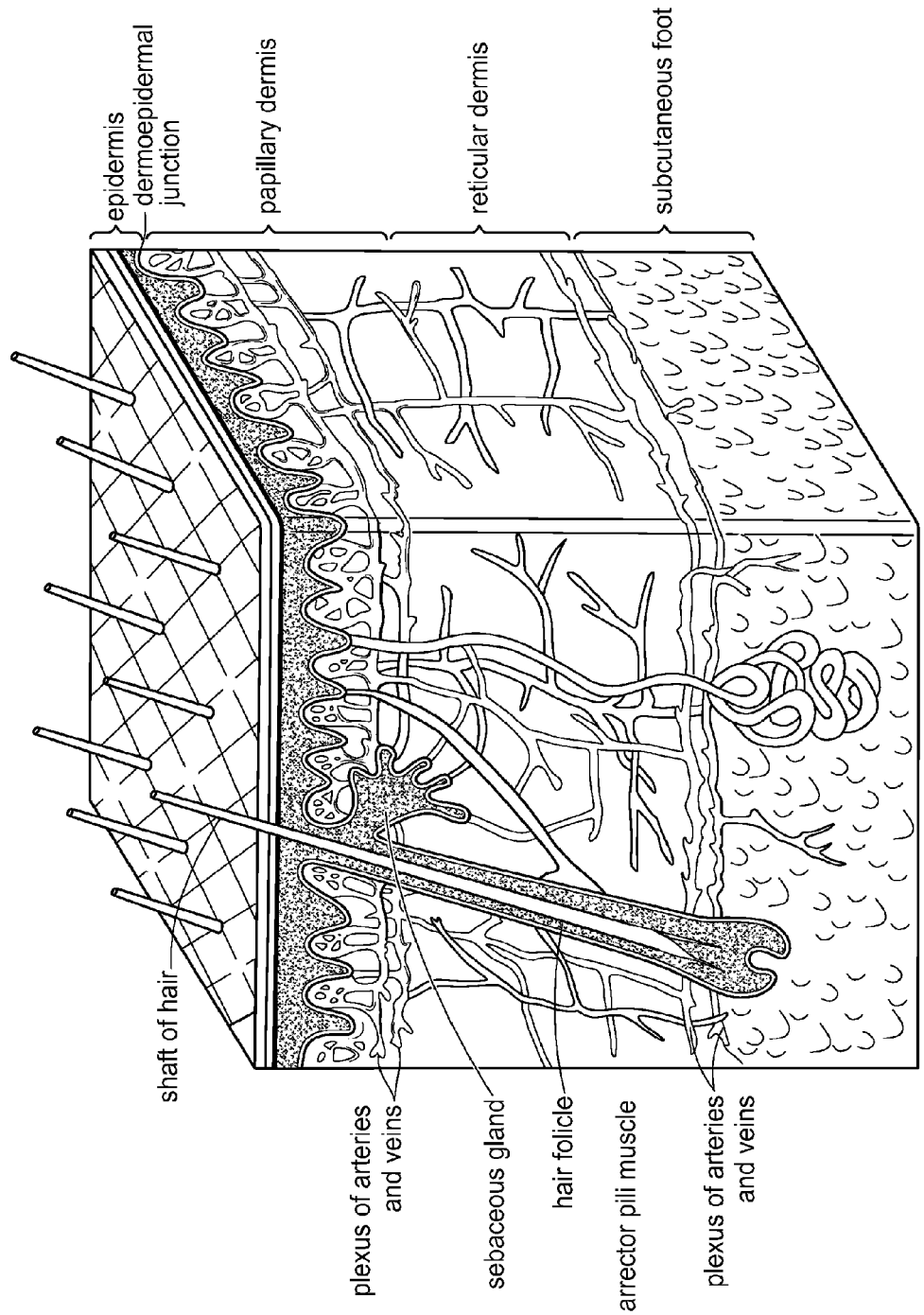
FIG. 1 is a drawing showing the anatomy of skin.

The skin consists of 2 layers. The outer layer, or epidermis, is derived from ectoderm, and the thicker inner layer, or dermis, is derived from mesoderm. The epidermis constitutes about 5% of the skin, and the remaining 95% is dermis. FIG. 1 provides a diagram showing the anatomy of skin. The skin varies in thickness depending on anatomic location, gender, and age of the individual. The epidermis, the more external of the two layers, is a stratified squamous epithelium consisting primarily of melanocytes and keratinocytes in progressive stages of differentiation from deeper to more superficial layers. The epidermis has no blood vessels; thus, it must receive nutrients by diffusion from the underlying dermis through the basement membrane, which separates the 2 layers.

The dermis is a more complex structure. It is composed of 2 layers, the more superficial papillary dermis and the deeper reticular dermis. The papillary dermis is thinner, including loose connective tissue that contains capillaries, elastic fibers, reticular fibers, and some collagen. The reticular dermis includes a thicker layer of dense connective tissue containing larger blood vessels, closely interlaced elastic fibers, and coarse, branching collagen fibers arranged in layers parallel to the surface. The reticular layer also contains fibroblasts, mast cells, nerve endings, lymphatics, and some epidermal appendages. Surrounding the components of the dermis is the gel-like ground substance composed of mucopolysaccharides (primarily hyaluronic acid), chondroitin sulfates, and glycoproteins.

In a graft, the characteristics of the donor site are more likely to be maintained after grafting to a recipient site as a function of the thickness of the dermal component of the graft. However, thicker grafts require more favorable conditions for survival due to the requirement for increased revascularization. It has been discovered, however, that a substantially epidermal graft according to the invention is more likely to adapt to the characteristics of the recipient site.

Figure 2A:
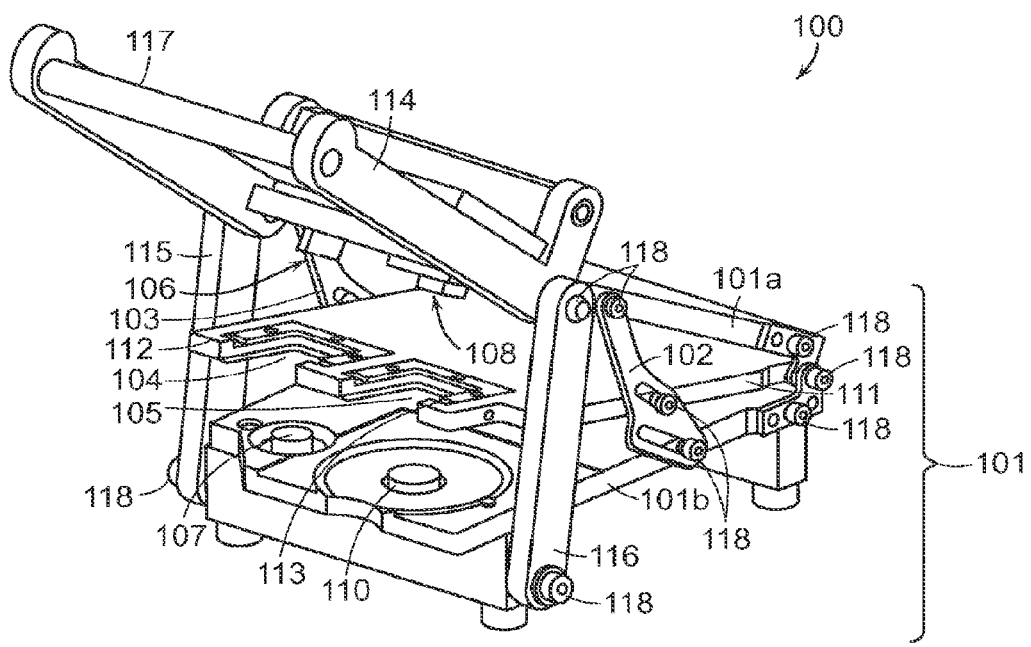
FIG. 2A shows an embodiment of devices of the invention. This figure shows the device in an open configuration.
Figure 3:
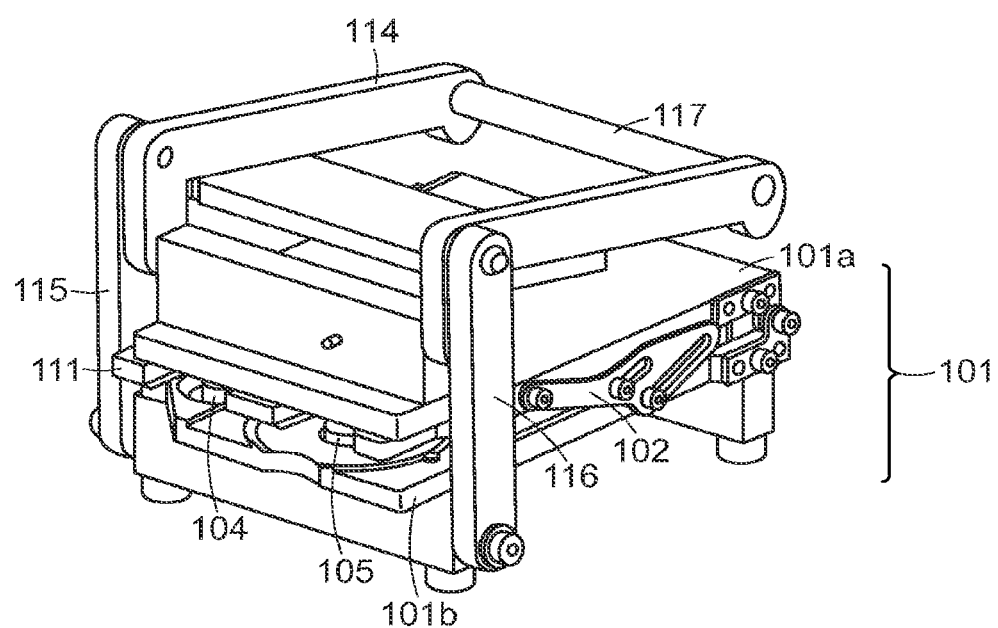
FIG. 3 shows the device of FIG. 2A in a closed configuration.

The invention generally relates to devices for generating and transferring micrografts and methods of use thereof. Reference is now made to FIG. 2A, which shows a device 100 of the invention. Device 100 includes a housing 101. The housing has a top portion 101a and a bottom portion 101b. The top portion 101a is hingedly connected to the bottom portion 101b. The housing 101 has an open configuration and a closed configuration. FIG. 2A shows the housing 101 in the open configuration. FIG. 3 shows the housing 101 in a closed configuration. The hinges are connected to device 100 by bolts 118.

Figure 8:
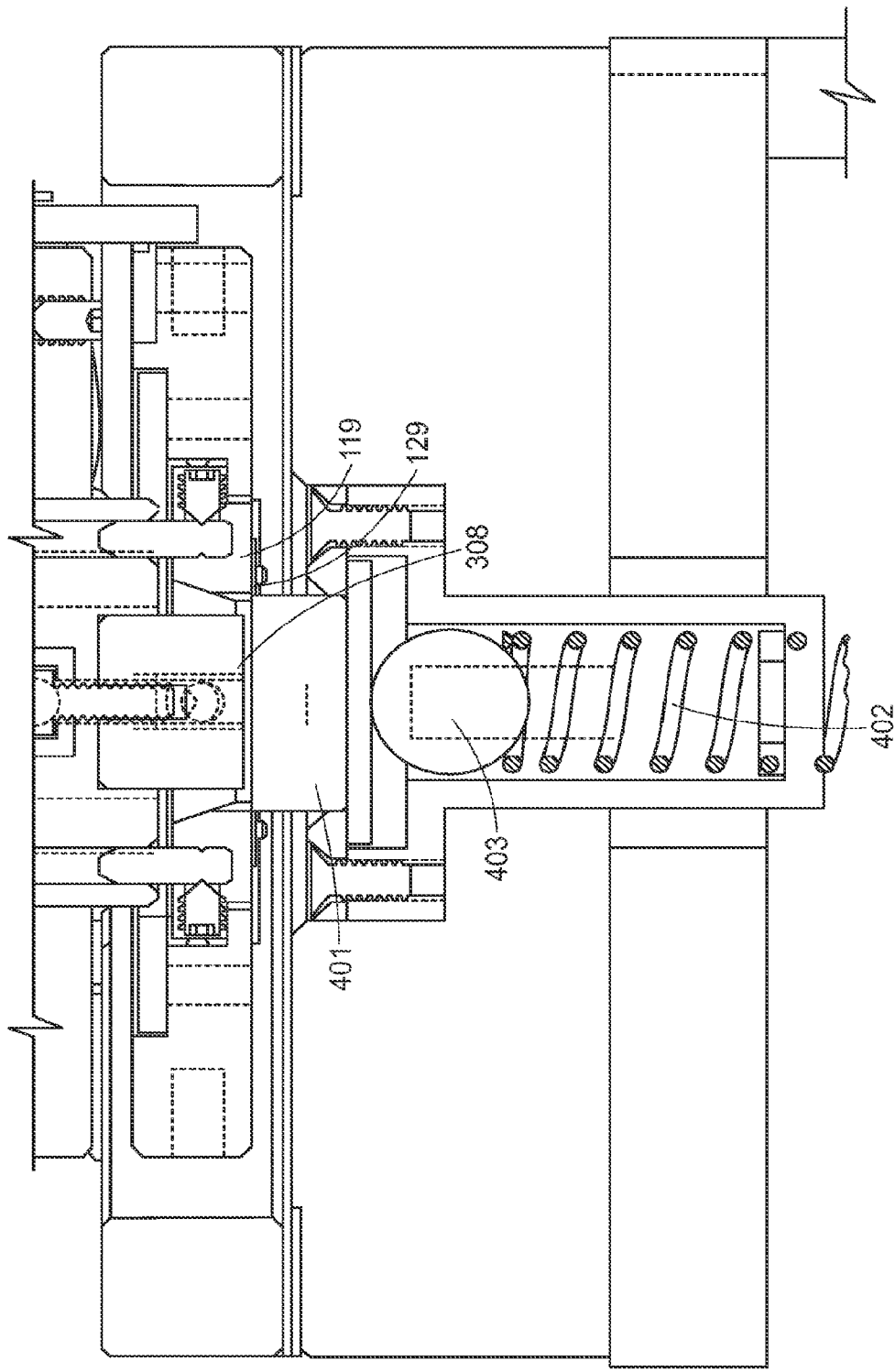
FIG. 8 shows the spring loaded base member of devices of the invention.

Device 100 further includes a micrograft generating station 104 and a micrograft transferring station 105. The micrograft generating station 104 includes a first member 106 connected to the top portion 101a of the housing 101, and a second member 107 connected to the bottom portion 101b of the housing 101. The first member 106 is aligned with the second member 107. The second member may be a spring loaded base that includes a stage 401, coupled to a spring 402 (FIG. 8). The spring loaded base may further include a ball 403 to focus the force on the center of the stage 401.

Figure 2B:
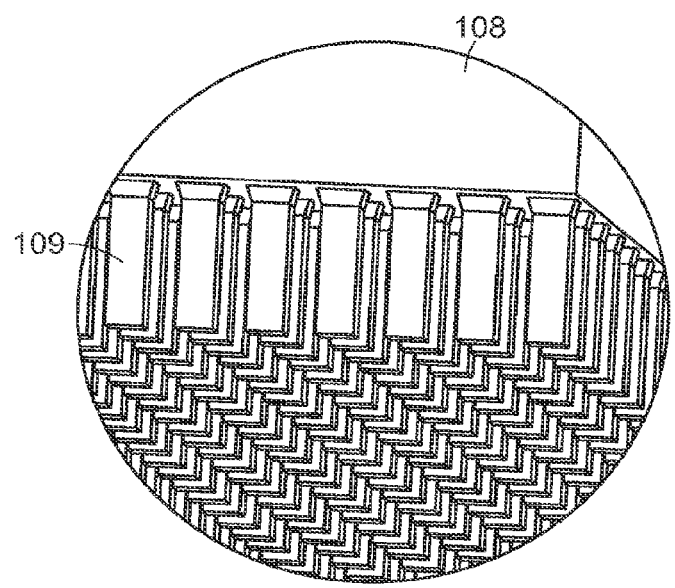
FIG. 2B is an enlarged view of the transfer pusher. This figure shows the plurality of prongs of the pusher.

The micrograft transferring station 105 includes a transfer pusher 108 including a plurality of prongs 109 (FIG. 2B). The transfer pusher 108 is connected to the top portion 101a of the housing 101 such that the prongs 109 are oriented downward toward the bottom portion 101b of the housing 101. The micrograft transferring station 105 further includes a transfer stage 110, which is connected to the bottom portion 101b of the housing 101. The transfer pusher 108 and the transfer stage 110 are aligned with each other. The transfer stage 110 may be made of any material that is softer than that of the transfer pusher 108. In certain embodiments, the transfer stage 110 is composed of a compressible material. In other embodiments, the second member 107 includes a spring loaded base (FIG. 8). The spring loaded base includes a stage 401, coupled to a spring 402. The spring loaded base may further include a ball 403 to focus the force on the center of the stage 401. The base is generally has a flat top and is made of a relatively hard material, i.e., not easily deformable or compressible.

Housing 101 further includes a cartridge receiving portion 111. The cartridge receiving portion 111 is located between the top portion 101a and the bottom portion 101b of the housing 101, and is also hingedly connected with the top portion 101a and the bottom portion 101b of the housing 101. The cartridge receiving portion 111 includes a first slot 112 and a second slot 113. The first slot 112 is aligned with the micrograft generating station 104 and the second slot 113 is aligned with the micrograft transferring station 105.

The housing 101 may further include members 102 and 103 that connect to the top portion 101a, the cartridge receiving portion 111, and the bottom portion 101b. Members 102 and 103 are movable and help control the position of the cartridge receiving portion 111 as device 100 is transformed from the open configuration to the closed configuration.

Device 100 also includes a lever 114 and linkage arms 115 and 116. The lever 114 is connected to the top portion 101a of the housing 101. The lever 114 may include a handle 117 that may be used to transform the device 100 from the open configuration to the closed configuration and back to the open configuration. Linkage arms 115 and 116 are connected to the lever 114, the top portion 101a of the housing 101, and bottom portion 101b of the housing 101. The linkage arms 115 and 116 act as force multipliers, such that upon engagement of the lever 114, an exponential amount of force is transferred to the micrograft generating station 104 and the micrograft transferring station 105 as an operator transforms device 100 from the open configuration to the closed configuration. The exponential amount of force transferred may be varied by varying the length of the lever 114 or the length of the linkage arms 115 and 116. In certain embodiments, the device 100 is configured to provide for at least about a 50×, e.g. about 100×, increase in force transferred to the micrograft generating station 104 as compared to the amount of force applied to the lever 114 by an operator to transform the device from the open configuration to the closed configuration.

Figure 4A:
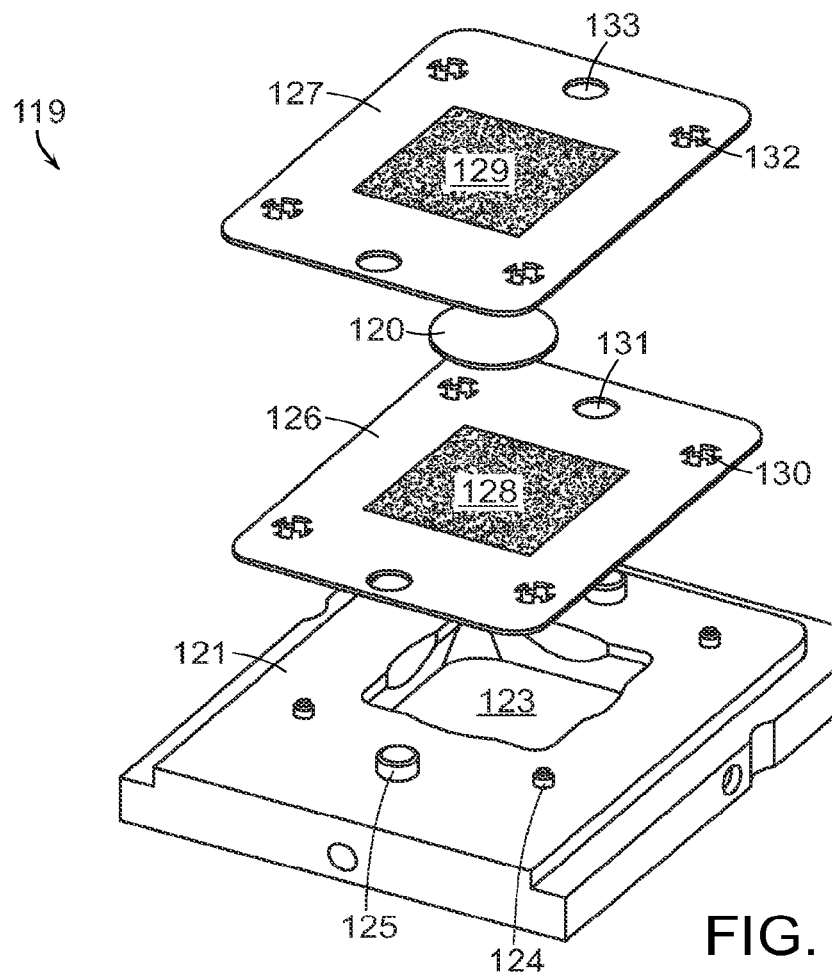
FIGS. 4A and 4B show a cartridge that is compatible with devices of the invention.
Figure 4B:
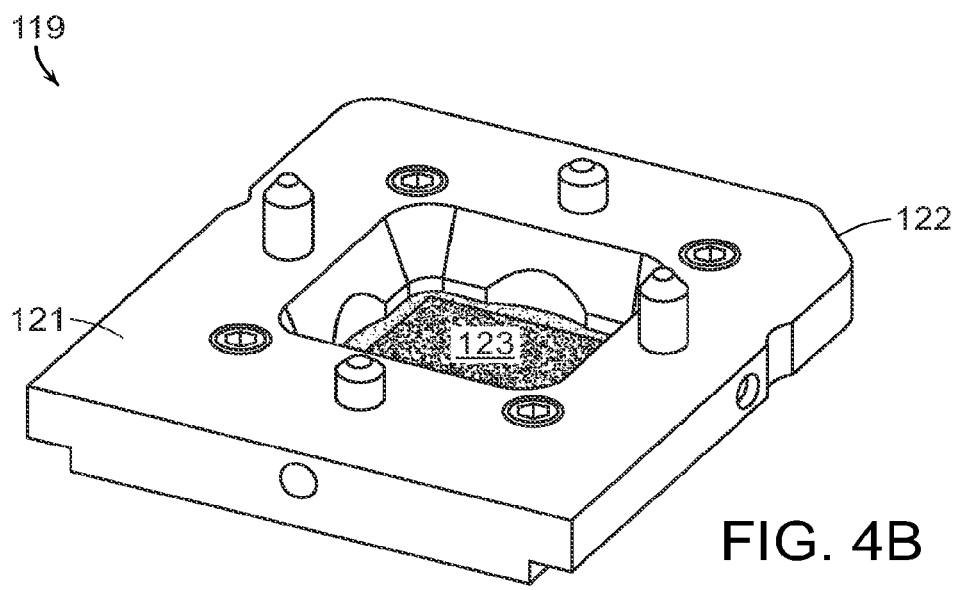

Reference is now made to FIGS. 4A and 4B, which show a cartridge 119. FIG. 4A shows an exploded view of the cartridge 119. FIG. 4B shows a fully assembled cartridge 119. The cartridge 119 is compatible with the first slot 112 and second slot 113 of the cartridge receiving portion 111 of the device 100, and is removable from the first and second slots 112 and 113 of the cartridge receiving portion 111 of the device 100. The cartridge 119 is configured to hold a skin graft 120.

The cartridge 119 includes a frame 121. It is noted that FIG. 4B shows the frame 121 of the cartridge 119 in the orientation in which it is inserted into the device 100. FIG. 4A shows the frame upside down. The frame 121 includes a beveled edge 122. The beveled edge 122 aligns with beveled edges of the first slot 112 and second slot 113 of the cartridge receiving portion 111 of the device 100, ensuring that the cartridge 119 is inserted into first slot 112 and second slot 113 with the proper orientation. The frame 121 also includes a hollow portion 123. Upon insertion of the cartridge 119 into the first and second slots 112 and 113, the hollow portion 123 is aligned with the first and second members 106 and 107 of the micrograft generating station 104 and is also aligned with the transfer pusher 108 and the transfer stage 110 of the micrograft transferring station 105.

Cartridge 119 further includes a first plate 126 and a second plate 127. The first plate 126 includes a mesh grid 128, and the second plate 127 includes a mesh grid 129. Once assembled, the mesh grid 128 of the first plate 126 and the mesh grid 129 of the second plate 127 are aligned with the hollow portion 123 of the frame 121, and holes of the mesh grid 128 of the first plate 126 are aligned with holes of the mesh grid 129 of the second plate 127. The holes in the grids 128 and 129 of the first and second plates 126 and 127 are sized to provide an array of micrografts of a desired size, such as lateral sizes between about 100 microns and about 1000 microns or about 300 microns to about 500 microns.

For example, for repigmenting skin tissue, the micrografts used may have a presence of melanocytes. Accordingly, a lateral dimension of such micrografts can be between less than about 1 mm, e.g., 200 to 1000 microns. Other exemplary sizes are between 400 and 800 microns. The area of the micrografts can be between about 0.04 mm$^2$ and about 1 mm$^2$. The exemplary sizes can provide micrografts large enough such that each micrograft is likely to contain some melanocytes, yet small enough to provide a large number of micrografts from a particular piece of graft tissue, which can facilitate a significant degree of expansion on the graft site.

For treating burns or ulcers, where presence and proliferation of keratinocytes is important, the micrograft sizes may be smaller. For example, a lateral dimension of micrografts containing keratinocytes can be between about 50 microns and about 1000 microns, or between 100 microns and about 800 microns. The area of such micrografts can be between about 0.0025 mm$^2$ and about 1 mm$^2$. The exemplary size ranges provide micrografts large enough to contain viable and undamaged keratinocytes, and small enough to facilitate repair of a larger area of damaged skin.

To ensure proper alignment, frame 121 includes plate retaining pins 124 and plate locating pins 125. First plate 126 includes plate retaining holes 130 and plate locating holes 131, and second plate 127 includes plate retaining holes 132 and plate locating holes 133. The plate retaining holes 130 and plate locating holes 131 of the first plate 126 are aligned with plate retaining pins 124 and plate locating pins 125 of frame 121. Similarly, plate retaining holes 132 and plate locating holes 133 of the second plate 127 are aligned with plate retaining pins 124 and plate locating pins 125 of frame 121. The alignment of the plate retaining holes 130 and plate locating holes 131 of the first plate 126, the plate retaining holes 132 and plate locating holes 133 of the second plate 127, and the plate retaining pins 124 and plate locating pins 125 of frame 121 ensures that once assembled, the mesh grid 128 of the first plate 126 and the mesh grid 129 of the second plate 128 are aligned with the hollow portion 123 of the frame 121, and the mesh grid 128 of the first plate 126 is aligned with the mesh grid 129 of the second plate 127.

The first plate 126 and the second plate 127 are removable from the frame 121. Removability allows for re-use of the frame 121. The skin graft 120 is inserted such that at least a portion of the graft 120 is aligned with the mesh grid 128 of the first plate 126 and the mesh grid 129 of the second plate 127.

In an alternative embodiment, cartridge retaining portion 111 of housing 101 includes only a single slot. In this embodiment, components of the micrograft generating station 104 (first and second members 105 and 106) and components of the micrograft transferring station 105 (transfer pusher 108 and transfer stage 110) are removable from housing 101. Thus, instead of transferring the cartridge 119 between first and second slots 112 and 113 that are aligned with a dedicated micrograft generating station 104 and a dedicated micrograft transferring station 105, the cartridge 119 remains in a single slot for the generating and transferring process, and it is the components of the micrograft generating station 104 and the micrograft transferring station 105 that are interchanged within the housing 101 depending on the whether an operator is generating micrografts or transferring micrografts.

Devices of the invention as described herein may be used to prepare skin grafts for any recipient site of damaged skin. Exemplary types of skin damage include burns (e.g., thermal or chemical), infections, wounds, or depigmentation. In particular embodiments, the recipient site is an area of depigmented skin that has been prepared to receive a skin graft.

General methods for preparing skin grafts are described in co-owned and co-pending U.S. patent application Ser. No. 12/851,621, the content of which is incorporated by reference herein in its entirety. In certain embodiments, methods of the invention generally involve harvesting a skin graft from a donor site, such as an epidermal graft, generating an array of micrografts from the single graft, placing the graft on a first substrate, expanding a distance between the micrografts on a first substrate, optionally transferring the micrografts from the first substrate to a second substrate, and applying the micrografts to a recipient site.

Harvesting of the skin grafts may be accomplished by any technique known in the art, and the technique employed will depend on the type of graft required (e.g., epidermal graft, split thickness graft, or full thickness graft). An epidermal graft refers to a graft that consists of substantially epidermal skin and does not include any substantial portion of the dermal layer. A split thickness graft refers to a graft that includes sheets of superficial (epithelial) and some deep layers (dermal) of skin. A full-thickness graft refers to a graft that includes all of the layers of the skin including blood vessels.

In certain embodiments, harvesting a skin graft involves raising a blister and cutting the blister. In certain embodiments, the blister may be a fluid-filled blister (e.g. a suction blister). In other embodiments, the blister is not fluid-filled. Any type of raised blister may be used with methods of the invention.

In certain embodiments, suction blister grafting is used. Suction blister grafting involves raising a blister, and then cutting off the raised blister. An exemplary suction blister grafting technique is shown in Awad, (Dermatol Surg, 34(9): 1186-1193, 2008), the content of which is incorporated by reference herein in its entirety. This article also shows various devices used to form suction blisters. A suction blister device is also described in Kennedy et al. (U.S. Pat. No. 6,071,247), the content of which is incorporated by reference herein in its entirety. An exemplary device is commercially available from Electronic Diversities (Finksburg, Md.).

A device for raising a suction blister typically operates by use of suction chambers that are attached to a patient's skin. An instrument typically contains a power source, a vacuum pump, temperature controls and all related controls to operate multiple suction chambers. The suction chambers are connected to the console by a flexible connection. Each of the chambers is controlled by a preset temperature control to provide an optimal skin warming temperature. Both chambers share an adjustable common vacuum source that affects all chambers equally.

Blister formation is accomplished by attaching the suction blister device to a patient's skin. Typically hook & loop fastener straps are used to keep the device in place. The chamber heating system provides a slight warming of an orifice plate of the device, which is in direct contact with the patient's skin surface. The application of a moderate negative pressure from the instrument console, to the chamber interior, causes the patients skin to be gently drawn through the opening(s) in the orifice plate. The results are typical suction blisters, approximately the size of the opening(s) in the orifice plate. The skin and blister area is generally not damaged and patient discomfort is minimal.

The negative pressure chamber is fabricated of mostly plastic components, with two removable threaded caps. The upper cap is fitted with a clear viewing lens so that the actual blister formation can be observed. The opposite end of the chamber is fitted with a removable orifice plate that is placed on the patient's skin. Since this plate is simply threaded onto the chamber end, multiple plates with different opening patterns can be interchanged as desired.

The interior of the device is warmed and illuminated by an array of low voltage incandescent lamps. This lamp array is controlled from the instrument console temperature controller, cycling as needed, to maintain the set point temperature. The heat from these lamps is radiated and conducted to the orifice plate, which then warms the patient's skin. The chamber is connected to the console via a composite vacuum and low voltage electrical system. Quick connections are used for the vacuum and electrical system to facilitate removal and storage.

The Negative Pressure Instrument console is a self-contained fan cooled unit which is designed to operate on 120 VAC 60 Hz power. Vacuum is supplied by an industrial quality diaphragm type vacuum pump, capable of a typical vacuum of 20 in Hg (0-65 kpa) at 0 CFM. An analog controller that is preset to 40° C. provides the temperature control for each suction chamber. This provides accurate control of the orifice plate temperature. The instrument console has internal adjustments that allow the user to recalibrate the temperature setting if desired. Other temperatures can be preset if desired. The front panel includes a vacuum gauge and vacuum bleeder adjustment to regulate the vacuum to both chambers. The console front panel also contains the connections for the chamber assemblies.

Once the suction blister is raised, it is cut by methods known in the art (see e.g., Awad, Dermatol Surg, 34(9):1186-1193, 2008). The skin graft 120 is then inserted into cartridge 119. Frame 121 is turned upside down, as is shown in FIG. 4A. First plate 126 is placed over frame 121. The plate retaining holes 130 and plate locating holes 131 of the first plate 126 are aligned with the plate retaining pins 124 and the plate locating holes 125 of the frame 121. Once aligned, the first plate 126 is placed onto the frame 121 such that the plate retaining pins 124 and the plate locating holes 125 of the frame 121 go through the plate retaining holes 130 and plate locating holes 131 of the first plate 126. Once placed on the frame 121, the mesh grid 128 is aligned with the hollow portion 123 of the frame 121.

The skin graft 120 is then placed on the mesh grid 128 of the first plate 126. The graft should be roughly centered on the mesh grid 128 (FIG. 4A). In certain embodiments, the graft 120 is placed on the grid such that a basal layer of the graft 120 is facing up. Epidermal skin includes a stratum corneum layer and a basal layer. The stratum corneum refers to the outermost layer of the epidermis, composed of large, flat, polyhedral, plate-like envelopes filled with keratin, which is made up of dead cells that have migrated up from the stratum granulosum. This layer is composed mainly of dead cells that lack nuclei. The thickness of the stratum corneum varies according to the amount of protection and/or grip required by a region of the body. In general, the stratum corneum contains 15 to 20 layers of dead cells, and has a thickness between 10 and 40 µm.

The basal layer (or stratum germinativum or stratum basale) refers to the deepest layer of the 5 layers of the epidermis. The basal layer is a continuous layer of live cells and can be considered the stem cells of the epidermis. These cells are undifferentiated and proliferative, i.e., they create daughter cells that migrate superficially, differentiating during migration. Keratinocytes and melanocytes are found in the basal layer.

For a graft to become integrated at a recipient site, the graft must be able to receive nutrients. Since the cells of the basal layer are live cells, orienting an epidermal graft such that the basal layer interacts with the recipient site allows the graft to receive nutrients, and thus remain viable. In contrast, since the cells of the stratum corneum are dead cells, orienting an epidermal graft such that the stratum corneum layer interacts with the recipient site prevents the graft from receiving nutrients, resulting in death of the graft tissue and graft failure. By placing the graft 120 on the cartridge 119 with the basal layer facing up, proper orientation of the graft 120 is maintained, ensuring that once applied to the skin, it is the basal layer of the graft 120 that interacts with the tissue of the recipient site. Thus, methods of the invention ensure that during the grafting process, the basal layer of a graft interacts with the recipient site of a patient, allowing for the graft to receive nutrients and thus remain viable.

Once the graft 120 has been placed on the first plate 126, the second plate 127 is placed on top of the graft 120, sandwiching the graft 120 between the first and second plates 126 and 127 (FIG. 4A). Second plate 127 is placed over frame 121. The plate retaining holes 132 and plate locating holes 133 of the second plate 127 are aligned with the plate retaining pins 124 and the plate locating holes 125 of the frame 121. Once aligned, the second plate 127 is placed onto the frame 121 such that the plate retaining pins 124 and the plate locating holes 125 of the frame 121 go through the plate retaining holes 132 and plate locating holes 133 of the second plate 127. Once placed on the frame 121, the mesh grid 129 is aligned with the hollow portion 123 of the frame 121, and the mesh grid 129 of the second plate 127 is aligned with the mesh grid 128 of the first plate 126. Additionally, the skin graft 120 is now sandwiched between the first and second plates 126 and 127. The mesh grid 128 of the first plate 126 and the mesh grid 129 of the second plate 127 are only separated by the thickness of the graft 120.

Figure 5A:
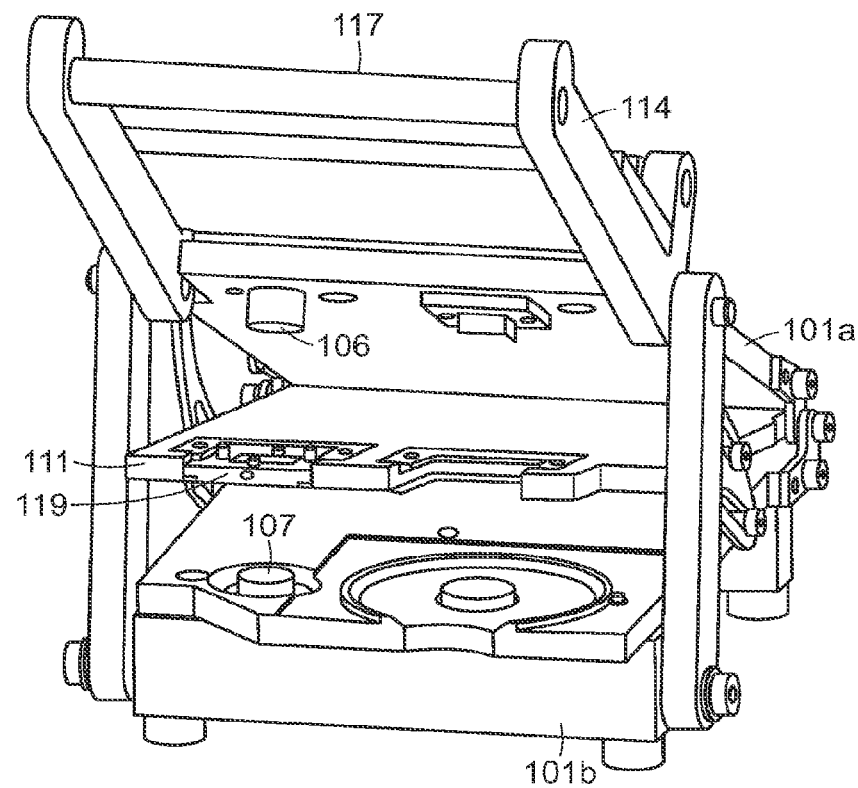
FIGS. 5A-5B show the process of generating the plurality of micrografts using devices of the invention.
Figure 5B:
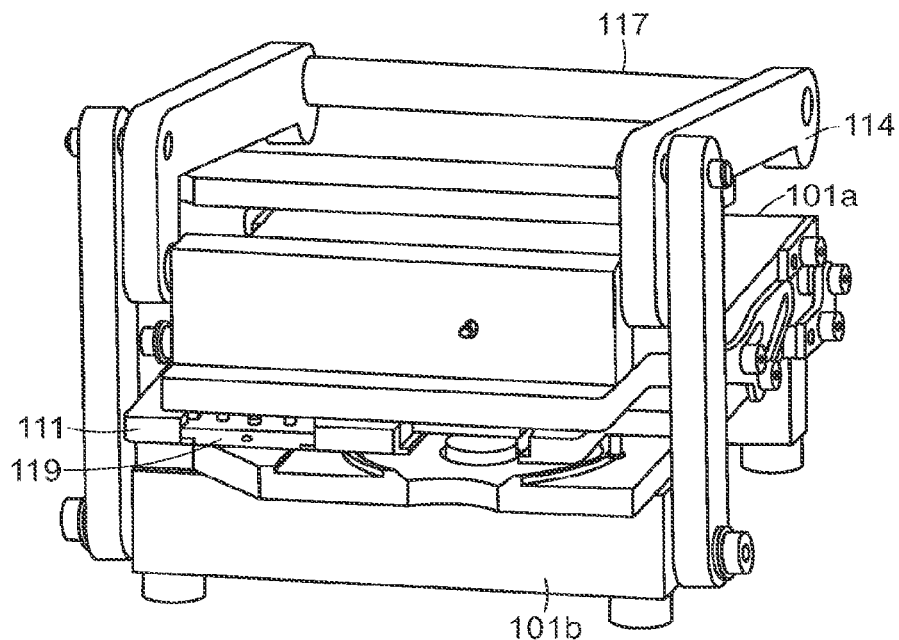
Figure 6A:
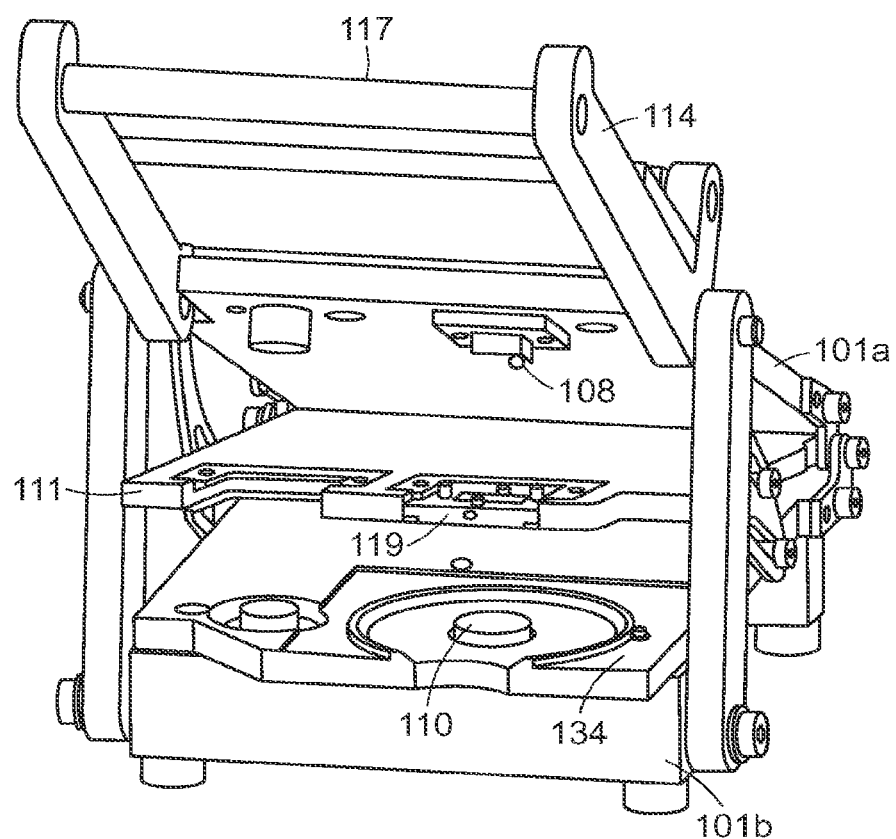
FIGS. 6A-6D show the process of transferring the plurality of micrografts to a substrate using devices of the invention.
Figure 6B:
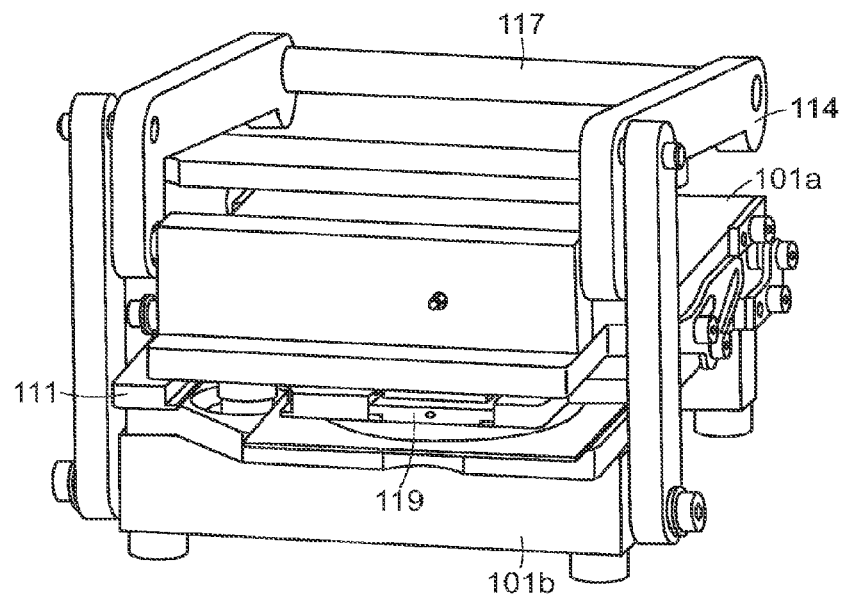
Figure 6C:
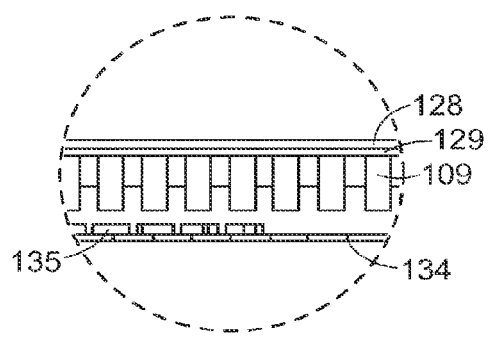
Figure 6D:
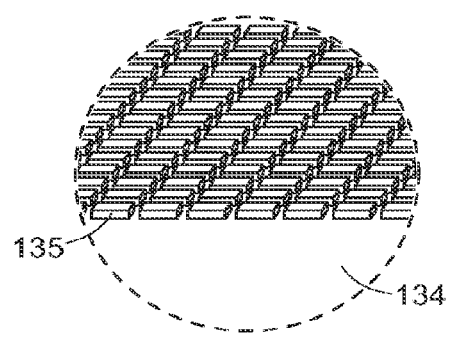

Now loaded into the cartridge, a plurality of micrografts may be generated from the single skin graft 120. To generate the micrografts, the cartridge 119 is flipped right side up and loaded into the micrograft generating station 104 of device 100. Reference is now made to FIGS. 5A-5B which show the process of generating the plurality of micrografts. Cartridge 119 is oriented such that bevel 122 on frame 121 of cartridge 119 is aligned with in first slot 112 of cartridge receiving portion 111 of housing 101. Once aligned, the cartridge 119 is slid into first slot 112. Once in slot 112, the hollow portion 123 of the frame 121 of the cartridge 119 is aligned with the first member 106 and the second member 107 of the micrograft generating station 104.

The device 100 is then transformed from the open configuration to the closed configuration by engaging lever 114, and moving the lever 114 from an open configuration to a closed configuration. Such movement causes the top portion 101a and the cartridge receiving portion 111 of the housing 101 to move vertically downward toward the bottom portion 101b of the housing 101. With such movement, the mesh grid 129 of the second plate 127 of the cartridge 119 come in contact with the second member 107 of the micrograft generating station 104. Additionally, the first member 106 of the micrograft generating station 104 passes into the hollow portion 123 of the frame 121 of cartridge 119 and contacts the mesh grid 128 of first plate 126 of the cartridge 119. The first and second members 106 and 107 compress the mesh grids 128 and 129 of first and second plates 126 and 127 of the cartridge 119. The compressive force results in the mesh grids 128 and 129 cutting the skin graft 120 that is sandwiched between plates 126 and 127, thereby generating the plurality of micrografts. The cuts may pass partially or completely through the graft tissue. The plurality of micrografts reside in the holes of the mesh grids 128 and 129.

Once the micrografts are generated, the lever 114 is moved from the closed configuration to the open configuration, transforming device 100 from the closed configuration to the open configuration. Cartridge 119 is removed from first slot 112 of cartridge receiving portion 111 of housing 101. The cartridge is now ready to be transferred to the micrograft transferring station 105.

Reference is now made to FIGS. 6A-6D which show the process of transferring the plurality of micrografts to a substrate. The cartridge 119 is inserted into the second slot 113 of cartridge receiving portion 111 of housing 101. Cartridge 119 is oriented such that bevel 122 on frame 121 of cartridge 119 is aligned with a bevel in second slot 113 of cartridge receiving portion 111 of housing 101. Once aligned, the cartridge 119 is slid into second slot 113. Once in slot 113, the hollow portion 123 of the frame 121 of the cartridge 119 is aligned with the transfer pusher 108 and the transfer stage 110 of the micrograft transferring station 105.

A substrate 134 is placed on top of transfer stage 110. Generally, the substrate 134 will have an adhesive side and the substrate 134 should be placed onto the transfer stage 110 such that the adhesive side of the substrate 134 is facing up. The substrate may be made from any material that is biocompatible. In certain embodiments, the substrate is biocompatible and made from a material that is capable of being stretched upon application of a moderate tensile force. Exemplary materials include medical dressings, such as TEGADERM (medical dressing, commercially available from 3M, St. Paul, Minn.) or DUODERM (medical dressing, commercially available from 3M, St. Paul, Minn.). The substrate may also be gas permeable.

In certain embodiments, substrate 134 includes an adhesive on one side that facilitates attachment of the micrografts to the substrates. The substrate material may have intrinsic adhesive properties, or alternatively, a side of the substrate may be treated with an adhesive material, e.g., an adhesive spray such as LEUKOSPRAY (Beiersdoerf GmbH, Germany).

In certain embodiments, the material of the substrate 134 is a deformable non-resilient material. A deformable non-resilient material refers to a material that may be manipulated, e.g., stretched or expanded, from a first configuration to a second configuration, and once in the second configuration, there is no residual stress on the substrate. Such materials may be stretched to an expanded configuration without returning to their original size. Such deformable non-resilient materials tend to be soft, stiff or both soft and stiff. Softness is measured on the durometer scale. An example of such a material is a soft polyurethane. A soft polyurethane is produced as follows. Polyurethanes in general usually have soft and hard segments. The hard segments are due to the presence of phenyl bridges. In a soft polyurethane, the phenyl bridge is switched out for an aliphatic, which is more flexible as its 6 carbon ring has no double bonds. Therefore, all the segments are soft. On the Durometer Scale, a soft polyethylene is rated about Shore 80A. Other materials suitable for use with methods of the invention include low density polyethylene, linear low density polyethylene, polyester copolymers, polyamide copolymers, and certain silicones.

The device 100 is then transformed from the open configuration to the closed configuration by engaging lever 114, and moving the lever 114 from an open configuration to a closed configuration. Such movement causes the top portion 101a and the cartridge receiving portion 111 of the housing 101 to move vertically downward toward the bottom portion 101b of the housing 101. With such movement, the mesh grid 129 of the second plate 127 of the cartridge 119 come in contact with the substrate 134 that is on top of the transfer stage 110 of the micrograft generating station 105. Additionally, the plurality of prongs 109 of the transfer pusher 108 of the micrograft generating station 105 pass into the hollow portion 123 of the frame 121 of cartridge 119. The prongs 109 are small than the holes of the mesh grids 128 and 129. The prongs pass through the holes of the mesh grids 128 and 129 and push the micrografts 135 residing in the holes of the mesh grids 128 and 129 through the mesh grids 128 and 129 and onto the substrate 134.

Once the micrografts 135 are transferred to substrate 134, the lever 114 is moved from the closed configuration to the open configuration, transforming device 100 from the closed configuration to the open configuration. Due to the adhesive layer of the substrate 134, after contact with the substrate 134, the plurality of micrografts 135 remain adhered to the substrate 134.

Once the micrografts 135 have been transferred to the substrate 134, the substrate is stretched or expanded, resulting in increased distance between the individual micrografts, moving them apart and resulting in production of a skin graft that can repair a recipient site that is larger than the donor site from which the grafts were obtained. In methods of the invention, the individual grafts themselves are not expanded, i.e., the graft tissue is not stretched; rather, stretching of the substrate increases the space or distance between each individual micrograft. Methods of the invention thus minimize tissue manipulation. Methods for expanding micrografts on a substrate are described for example in U.S. patent application Ser. No. 12/851,621, the content of which is incorporated by reference herein in its entirety.

The purpose of such processing is to use tissue from a donor site to cover a wound area that is larger than the donor site. The stretching of the substrate may be done manually, i.e., by hand, or may be done with the help of a machine. The stretching may be substantially uniform in all directions or may be biased in a certain direction. In a particular embodiment, the stretching is substantially uniform in all directions. Stretching of the substrate may be performed mechanically or may be accomplished by application of a pressurized fluid or gas. In certain embodiments, air pressure is used to expand the first substrate. Exemplary devices and methods are described in Korman (U.S. Pat. No. 5,914,264), the content of which is incorporated by reference herein in its entirety.

Any minimum distance can be provided between micrografts after the first substrate is stretched. The amount of stretching can be large enough to provide a sufficiently large area of substrate containing micrografts to allow a larger area of damaged tissue to be repaired using a particular amount of graft tissue removed from the donor site, i.e., the area of the stretched first substrate containing the separated micrografts can be much larger than the total area of the donor site. For example, the distance between adjacent micrografts on the stretched first substrate can be greater than about 0.5 mm, although small separation distances may also be used. For repigmentation of skin tissue, an amount of stretching can be applied to the first substrate such that the distance between adjacent micrografts is less than about 4 mm, because it is known that melanocytes, when grafted to a depigmented region, can migrate up to about 2 mm from each micrograft to repigment regions between the micrografts. This average distance can be larger if keratinocyte migration is involved with the tissue being treated because keratinocytes typically migrate greater distances compared to melanocytes.

The ratio of the wound area to the donor site area is referred to as the expansion ratio. A higher expansion ratio is desirable to minimize the trauma of the donor site, and to aid patients who have only a small amount of tissue available for grafting purposes. The amount of area expansion, e.g., the ratio of an area of damaged tissue that can be repaired compared to an area of graft tissue removed from a donor site, may be 500× or more. In particular embodiments, the area of expansion may be from about 10× to about 100×, which provides a more uniform coverage and/or repigmentation of the recipient site. For repairing burns or ulcerated tissue, the micrografts may be smaller than those used to repair other types of damaged tissue, and thus the distances between adjacent micrografts may be greater after stretching of the first substrate. In such an exemplary application, an area expansion of about 1000× or more may be used.

In other embodiments and depending on the material of the substrate 134, maintaining the substrate 134 in a stretched configuration may result in stress on the substrate 134 that is not optimal. Additionally, the stretched substrate 134 may not retain the same properties as the unstretched configuration of the substrate 134, i.e., technological characteristics, such as physical, environmental and performance characteristics could be affected by the stretching of the substrate 134. Additionally, methods used to maintain the substrate 134 in its stretched condition may be physically cumbersome and prevent uniform application of the micrografts to uneven skin surfaces. Thus in certain embodiments, once the substrate 134 has been stretched, the spaced apart micrografts are transferred to a second substrate. By transferring the micrografts to a second substrate, methods of the invention minimize manipulation and stress of the substrate that holds the graft to the recipient site.

After stretching the substrate 134, the second substrate is brought into contact with the grafts on the stretched substrate 134. Transfer is facilitated by the second substrate having greater affinity or more adhesive force toward the micrografts than the substrate 134. In certain embodiments, the second substrate is coated with a hydrocolloid gel. In other embodiments, the substrate 134 is wetted with a fluid such as water or a saline solution. Wetting the micrografts and the substrate 134 provides lubrication between the grafts and the substrate 134 and allows for easy transfer of the grafts from the substrate 134 to the second substrate. After wetting the substrate 134, the grafts have greater affinity for the second substrate than the substrate 134. The wetted substrate 134 is then removed from the second substrate and the grafts remain attached to the second substrate. The distance between the micrografts is maintained after transfer of the micrografts from the stretched substrate 134 to the second substrate.

The second substrate may be made from any material known in the art that is compatible with biological tissue. The second substrate may also be capable of being stretched upon application of a moderate tensile force. Exemplary materials for the second substrates include medical dressings, such as TEGADERM (medical dressing, commercially available from 3M, St. Paul, Minn.) or DUODERM (medical dressing, commercially available from 3M, St. Paul, Minn.). The second substrate may also be gas permeable.

In certain embodiments, the second substrate includes an adhesive on one side that facilitates attachment of the grafts to the second substrate. The second substrate material may have intrinsic adhesive properties, or alternatively, a side of the second substrate may be treated with an adhesive material, e.g., an adhesive spray such as LEUKOSPRAY (Beiersdoerf GmbH, Germany). In certain embodiments, the substrate 134 and the second substrates are the same material. In other embodiments, the substrate 134 and second substrate are different materials. In certain embodiments, the materials of substrate 134 and the second substrate are chosen to facilitate transfer of the micrografts from the substrate 134 to the second substrate. For example, in certain embodiments, the material chosen for substrate 134 has a weaker adhesive than the material chosen for the second substrate.

In certain embodiments, the material of substrate 134 is a deformable non-resilient material as discussed above. Such materials may be stretched to an expanded configuration without returning to their original size, and thus in these embodiments it is not necessary to transfer the micrografts from substrate 134 to a second substrate. Instead, the substrate 134 including the micrografts is applied to a recipient site.

Ultimately, the grafts and substrate are applied to a recipient of site of a patient. Prior to applying the grafts to the recipient site, the site is prepared to receive the grafts using any technique known in the art. Necrotic, fibrotic or avascular tissue should be removed. The technique used to prepare the site will depend on damage to the recipient site. For example, epidermal tissue, if present at the recipient site, can be removed to prepare the area for receiving the micrografts. Burned or ulcerated sites may not need removal of epidermal tissue, although some cleaning of the site or other preparation of the site may be performed. Wounds should be debrided and then allowed to granulate for several days prior to applying the graft. Most of the granulation tissue should be removed since it has a tendency to harbor bacteria. Applying silver sulfadiazine to the wound for 10 days prior to grafting reduces the bacterial count greatly.

The size of the area at the recipient site can be about the same size as the area of the stretched substrate 134 having micrografts 135 adhered thereto. This size generally will be greater than the area of the original graft tissue that was removed from the donor site to form the micrografts. The depigmented or damaged skin can be dermabraded with sandpaper or another rough material. Alternatively, the epidermal tissue can be removed from the recipient site by forming one ore more blisters over the area to be treated, e.g., a suction blister or a freezing blister, and the raised epidermal blister tissue can then be removed by cutting or another procedure.

The substrate having the micrografts can be placed over the area to be treated to form a dressing. A portion of the substrate having the micrografts can be positioned over the area to be repaired, e.g., the area from which the epidermal tissue has been abraded or removed for repigmentation. The substrate can be fixed in place over the treatment area, e.g., using tape or the like. The substrate can be removed after sufficient time has elapsed to allow attachment and growth of the micrografts in the treatment area, e.g., several days to a few weeks.

Figure 7:
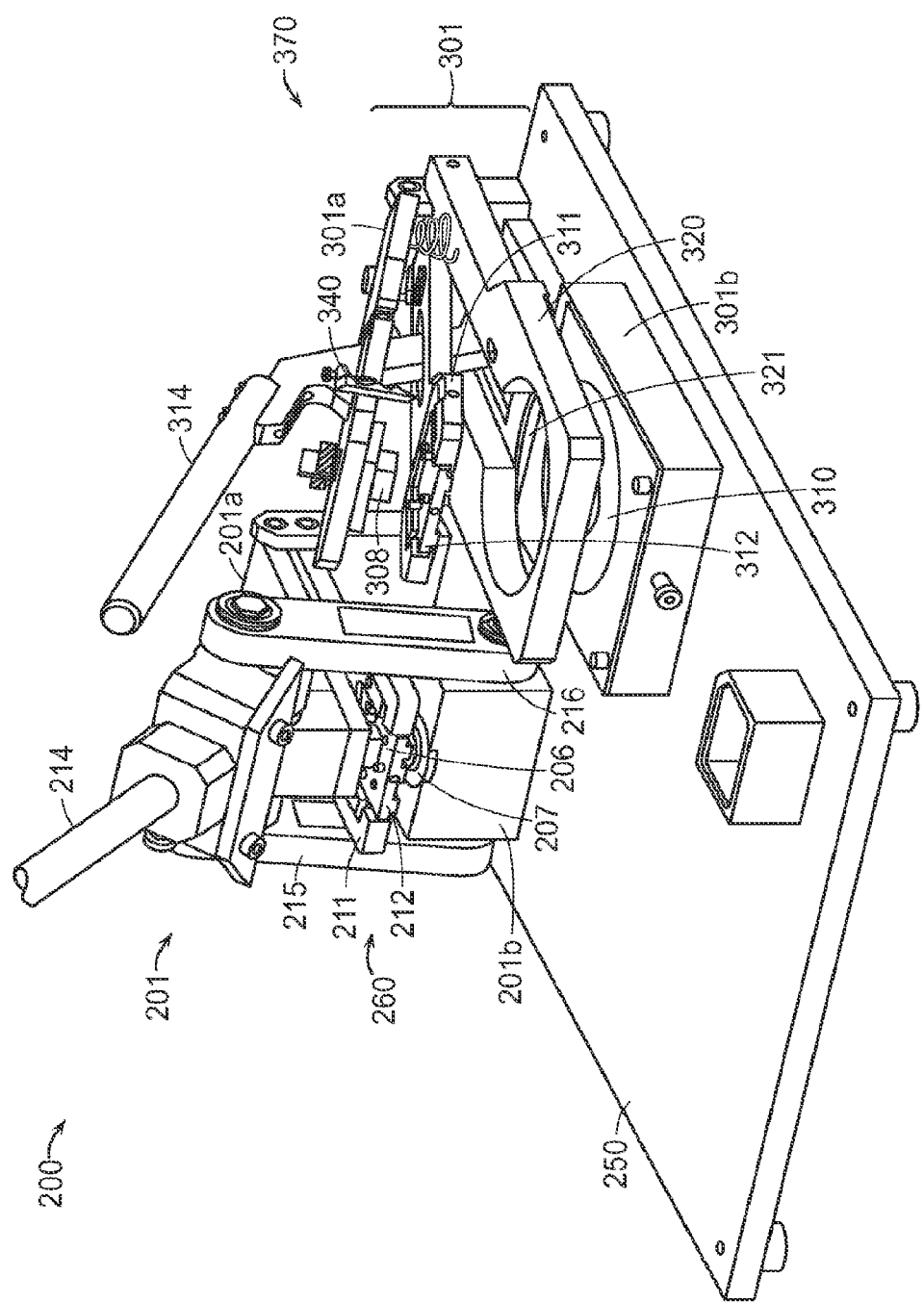
FIG. 7 shows another embodiment of devices of the invention.

Reference is now made to FIG. 7, which shows a device 200 of the invention. Device 200 includes a base member 250, a micrograft generating station 260 integrated with the base member 250, and a micrograft transferring station 370 integrated with the base member 250. Integration of the micrograft generating station and the micrograft transferring station with the base member can be as a single unitary device or can be such that the micrograft transferring station and the micrograft generating station are removably coupled to the base member. In certain embodiments, the micrograft generating station and the micrograft transferring station are removed from the base member and are used as individual stand-alone devices.

The micrograft generating station 260 comprises a frame 201. The frame has a top portion 201*a* and a bottom portion 201*b*. The top portion 201*a* is connected to the bottom portion 201*b*. The frame 201 has an open configuration and a closed configuration. FIG. 7 shows the frame 201 in the closed configuration. The micrograft generating station 260 further includes a first member 206 connected to the top portion 201*a* of the frame 201, and a second member 207 connected to the bottom portion 201*b* of the frame 201. The first member 206 is aligned with the second member 207.

In certain embodiments, the second member 207 includes a spring loaded base (FIG. 8). The spring loaded base includes a stage 401, coupled to a spring 402. The spring loaded base may further include a ball 403 to focus the force on the center of the stage 401.

Frame 201 further includes a cartridge receiving portion 211. The cartridge receiving portion 211 is located between the top portion 201*a* and the bottom portion 201*b* of the frame 201, and is also connected with the top portion 201*a* and the bottom portion 201*b* of the frame 201. The cartridge receiving portion 211 includes a slot 212. The slot 212 is aligned with the first and second members of the micrograft generating station 260. In this figure, slot 212 is shown with a the cartridge 119 loaded into the slot 212.

The micrograft generating station 260 also includes a lever 214. The lever 214 is connected to the top portion 201*a* of the frame 201. The lever 214 is used to transform the micrograft generating station 260 from the open configuration to the closed configuration and back to the open configuration. Linkage arms 215 and 216 are connected to the lever 214, the top portion 201*a* of the frame 201, and bottom portion 201*b* of the frame 201. The linkage arms 215 and 216 act as force multipliers, such that upon engagement of the lever 214, an exponential amount of force is transferred to the micrograft generating station 260 as an operator transforms micrograft generating station 260 from the open configuration to the closed configuration. The exponential amount of force transferred may be varied by varying the length of the lever 214 or the length of the linkage arms 215 and 216. In certain embodiments, the micrograft generating station 260 is configured to provide for at least about a 50× increase in force transferred to the micrograft generating station 260 as compared to the amount of force applied to the lever 214 by an operator to transform the micrograft generating station 260 from the open configuration to the closed configuration.

The micrograft transferring station 370 comprises a frame 301. The frame has a top portion 301*a* and a bottom portion 301*b*. The top portion 301*a* is connected to the bottom portion 301*b*. The frame 301 has an open configuration and a closed configuration. FIG. 7 shows the frame 301 in the open configuration. The micrograft transferring station 370 further includes a transfer pusher 308 including a plurality of prongs 309. The prongs are similar to those shown in FIG. 2B. The transfer pusher 308 is connected to the top portion 301a of the frame 301 such that the prongs 309 are oriented downward toward the bottom portion 301b of the frame 301. The micrograft transferring station 370 further includes a transfer stage 310, which is connected to the bottom portion 301b of the frame 301. The transfer pusher 308 and the transfer stage 310 are aligned with each other. In certain embodiments, the transfer stage 310 may be made of any material that is softer than that of the transfer pusher 308. In certain embodiments, the transfer stage 310 is composed of a compressible material. In other embodiments, the transfer stage 310 includes a spring loaded base (FIG. 8). The spring loaded base includes a stage 401, coupled to a spring 402. The spring loaded base may further include a ball 403 to focus the force on the center of the stage 401.

Frame 301 further includes a cartridge receiving portion 311. The cartridge receiving portion 311 is located between the top portion 301a and the bottom portion 301b of the frame 301, and is also hingedly connected with the top portion 301a and the bottom portion 301b of the frame 301. The cartridge receiving portion 311 includes a slot 312. The slot 312 is aligned with transfer pusher and the transfer stage of the micrograft transferring station 370. In this figure, slot 312 is shown with a the cartridge 119 loaded into the slot 312.

Frame 301 further includes a stripper plate 320. The stripper plate 320 is located above the bottom portion 301b of the frame 301 and below the cartridge receiving portion 311 and the top portion 301a of the frame 301. The stripper plate 320 includes an inner hollow portion 321 such that the cartridge receiving portion 311, the transfer pusher transfer pusher 308 and the transfer stage 310 fit within the inner hollow portion 321 of the stripper plate 320. Such configuration is important for transfer of micrografts from the cartridge to the substrate, which is described in greater detail below.

The micrograft transferring station 370 also includes a lever 314. The lever 314 runs through the center of frame 301 and is connected to the top portion 301a, the cartridge receiving portion 311, the stripper plate 320, and the bottom portion 301b. The lever 314 is used to transform the micrograft transferring station 370 from the open configuration to the closed configuration and back to the open configuration. The lever 314 acts as a force multiplier, such that upon engagement of the lever 314, an exponential amount of force is transferred to the micrograft transferring station 370 as an operator transforms micrograft transferring station 370 from the open configuration to the closed configuration. The exponential amount of force transferred may be varied by varying the length of the lever 314. In certain embodiments, the lever 314 is configured to provide for at least about a 50× increase in force transferred to the micrograft transferring station 370 as compared to the amount of force applied to the lever 314 by an operator to transform the micrograft transferring station 370 from the open configuration to the closed configuration.

Cartridges that may be used with device 200 are the same as those described above in connection with device 100.

Device 200 as described herein may be used to prepare skin grafts for any recipient site of damaged skin. General methods for preparing skin grafts are described in co-owned and co-pending U.S. patent application Ser. No. 12/851,621, the content of which is incorporated by reference herein in its entirety. In certain embodiments, methods of the invention generally involve harvesting a skin graft from a donor site, such as an epidermal graft, generating an array of micrografts from the single graft, placing the graft on a first substrate, expanding a distance between the micrografts on a first substrate, optionally transferring the micrografts from the first substrate to a second substrate, and applying the micrografts to a recipient site. Harvesting of the skin grafts and placing of the harvested skin graft into a cartridge for use with device 200 is described above.

Now loaded into the cartridge, a plurality of micrografts may be generated using device 200. To generate the micrografts, the cartridge 119 is flipped right side up and loaded into the micrograft generating station 260 of device 200. Cartridge 119 is oriented such that bevel 122 on frame 121 of cartridge 119 is aligned with a bevel in slot 212 of cartridge receiving portion 211 of frame 201. Once aligned, the cartridge 119 is slid into slot 212. Once in slot 212, the hollow portion 123 of the frame 121 of the cartridge 119 is aligned with the first member 206 and the second member 207 of the micrograft generating station 260.

The micrograft generating station 260 is then transformed from the open configuration to the closed configuration by engaging lever 214. Such movement causes the top portion 201a and the cartridge receiving portion 211 of the frame 201 to move vertically downward toward the bottom portion 201b of the frame 201. With such movement, the mesh grid 129 of the second plate 127 of the cartridge 119 come in contact with the second member 207 of the micrograft generating station 260. Additionally, the first member 206 of the micrograft generating station 260 passes into the hollow portion 123 of the frame 121 of cartridge 119 and contacts the mesh grid 128 of first plate 126 of the cartridge 119. The first and second members 206 and 207 compress the mesh grids 128 and 129 of first and second plates 126 and 127 of the cartridge 119. The compressive force results in the mesh grids 128 and 129 cutting the skin graft 120 that is sandwiched between plates 126 and 127, thereby generating the plurality of micrografts. The cuts may pass partially or completely through the graft tissue. The plurality of micrografts reside in the holes of the mesh grids 128 and 129.

Once the micrografts are generated, the lever 214 is used to transform the micrograft generating station 260 back to the open configuration. Cartridge 119 is removed from slot 212 of cartridge receiving portion 211 of frame 201. The cartridge is now ready to be transferred to the micrograft transferring station 370.

Using micrograft transferring station 370, the micrografts are transferred to a substrate, as described here. The cartridge 119 is inserted into the 312 of cartridge receiving portion 311 of frame 301. Cartridge 119 is oriented such that bevel 122 on frame 121 of cartridge 119 is aligned with a bevel in slot 313 of cartridge receiving portion 311 of frame 301. Once aligned, the cartridge 119 is slid into slot 313. Once in slot 313, the hollow portion 123 of the frame 121 of the cartridge 119 is aligned with the transfer pusher 308 and the transfer stage 310 of the micrograft transferring station 370.

A substrate 134 is placed on top of transfer stage 310. Generally, the substrate 134 will have an adhesive side and the substrate 134 should be placed onto the transfer stage 310 such that the adhesive side of the substrate 134 is facing up. Further description of types of substrates to me used with devices of the invention is provided above.

The micrograft transferring station 370 is then transformed from the open configuration to the closed configuration by engaging lever 314. Engagement of the lever results in movement that causes the top portion 301a, the cartridge receiving portion 311, and the stripper plate 320 to move vertically downward toward the bottom portion 301b of the frame 301. With such movement, the stripper plate 320 moves downward and contacts the outer perimeter of the substrate 134. The hollow inner portion 321 surrounds that transfer stage 310 and leaves the transfer stage 310 accessible to interact with the cartridge 119. Then, the cartridge receiving portion 311 and the transfer pusher 308 move downward and into the hollow inner portion 321 of the stripper plate 320, resulting in the mesh grid 129 of the second plate 127 of the cartridge 119 coming in contact with the substrate 134 that is on top of the transfer stage 310 of the micrograft transferring station 370.

As this is occurring, the plurality of prongs 309 of the transfer pusher 308 of the micrograft transferring station 370 pass into the hollow portion 123 of the frame 121 of cartridge 119. The prongs 309 are small than the holes of the mesh grids 128 and 129. The prongs pass through the holes of the mesh grids 128 and 129 and push the micrografts 135 residing in the holes of the mesh grids 128 and 129 through the mesh grids 128 and 129 and onto the substrate 134. Once the micrografts 135 are transferred to substrate 134, the lever 314 is used to transform micrograft transferring station 370 back to the open configuration.

Figure 9:
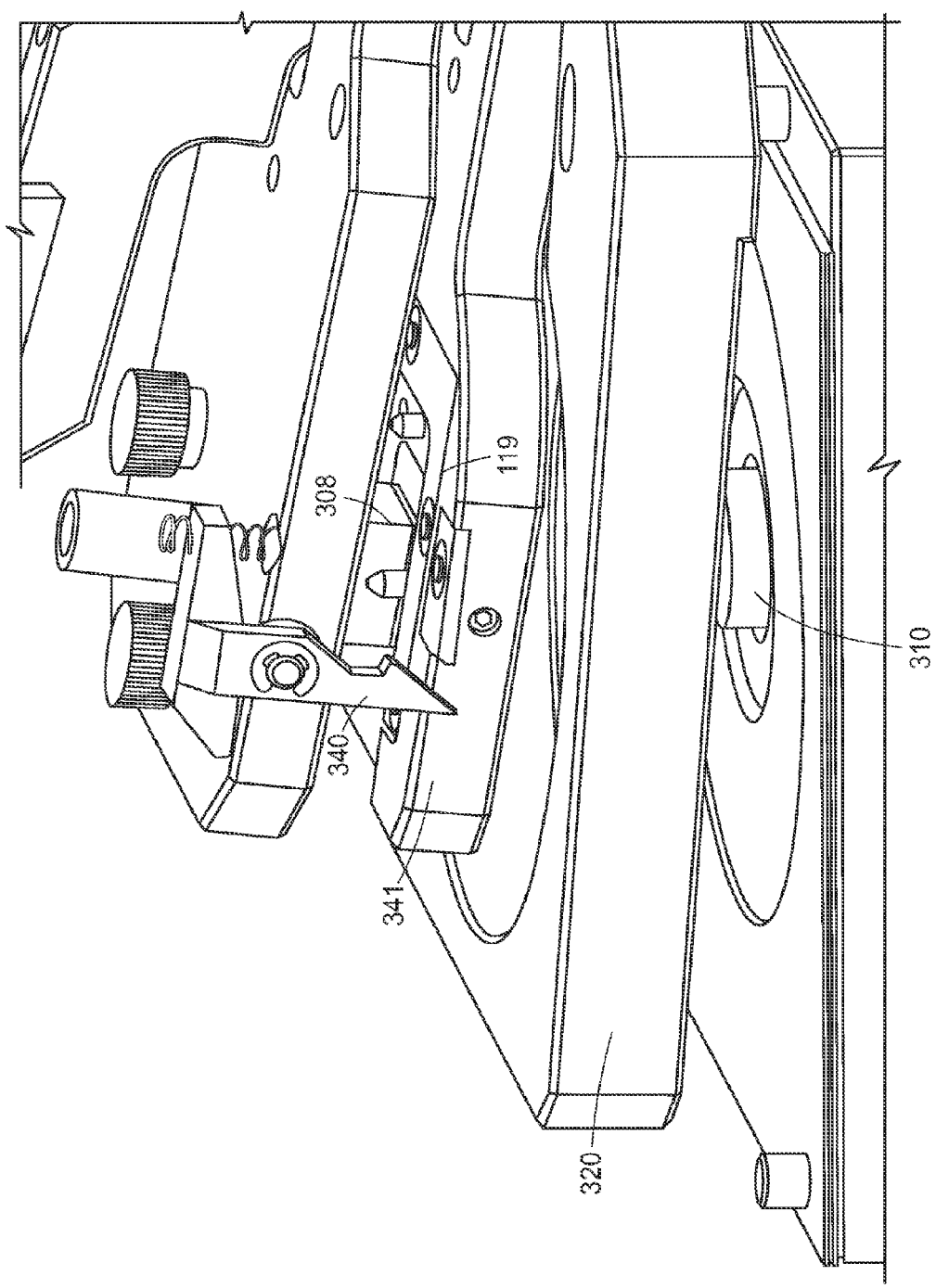
FIG. 9 shows a latch that links a top portion of a frame to a cartridge receiving portion of devices of the invention.

In greater detail, the mesh grid 129 holding the tissue is the first component to contact the substrate 134 on the transfer stage 310. The grid 129, the pusher 308, and the transfer stage move downward together a small amount before the cartridge receiving portion 311 that is holding the cartridge 119 holding the mesh grid 129 hits a stop. The prongs 309 of the pusher 308 continue pushing the tissue held in the grid 129 and the transfer stage 310 downward until the top portion 301a of the frame 301 hits a second stop. At this point, the micrografts 135 have been pushed through the grid 129 and onto the substrate 134 and the micrografts 135 are no longer in contact with the grid 129. Just prior to the pusher 310 hitting the second stop, a latch 340 on the top portion 301a interacts with a hasp 341 on the cartridge receiving portion 311, locking the top portion 301a to the cartridge receiving portion 311 so that their upward movement is linked (FIGS. 7 and 9). The lever 314 is then reengaged to transform the micrograft transferring station 370 back to the open configuration. This results in the pusher top portion 301a and linked cartridge receiving portion 311 to move upward until there is no longer contact with the substrate 134, leaving the micrografts fully transferred to the substrate 134. During this process, the stripper plate 320 also moves upward, releasing itself from the edges of the substrate 134.

Once the micrografts 135 have been transferred to the substrate 134, the substrate is stretched or expanded, the micrografts are optionally transferred to a second substrate, and the expanded micrografts are applied to a recipient site, all of which is described above.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for generating and transferring micrografts, the method comprising:
    providing a device comprising a housing having an open configuration and a closed configuration; a micrograft generating station; and a micrograft transferring station;
    obtaining a cartridge comprising a frame having a hollow inner portion, a removable first plate comprising a mesh grid, and a removable second plate comprising a mesh grid;
    inserting a skin graft between the first and the second removable plates such that the skin graft is aligned with the mesh grids in the first and the second removable plates;
    inserting the cartridge into the micrograft generating station;
    engaging the micrograft generating station, thereby generating a plurality of micrografts; and
    engaging the micrograft transferring station, thereby transferring the plurality of micrografts to a substrate.

2. The method according to claim 1, wherein the cartridge in an assembled configuration, the mesh grid of the first removable plate and the mesh grid of the second removable plate are aligned with the hollow inner portion of the frame, and the mesh grid of the first plate is aligned with the mesh grid of the second removable plate.

3. The method according to claim 2, wherein engaging the micrograft generating station comprises:
    inserting the cartridge into the micrograft generating station of the device while the housing is in the open configuration; and
    transforming the housing from the open configuration to the closed configuration, thereby generating the plurality of micrografts.

4. The method according to claim 2, wherein engaging the micrograft transferring station comprises:
    inserting the cartridge into the micrograft transferring station of the device while the housing is in the open configuration;
    inserting the substrate below the cartridge; and
    transforming the housing from the open configuration to the closed configuration, thereby transferring the plurality of micrografts to the substrate.

5. The method according to claim 4, wherein the substrate is a medical dressing.

6. The method according to claim 1, wherein the graft is an autograft.

7. The method according to claim 1, further comprising prior to the providing step:
    harvesting the skin graft.

8. The method according to claim 7, wherein harvesting comprises:
    raising a blister; and
    cutting the blister to obtain the skin graft.

9. The method according to claim 8, wherein said step of raising a blister comprises:
    contacting a harvesting device having a hole to skin; and
    applying heat and/or vacuum pressure, thereby raising the blister.

10. The method according to claim 1, further comprising:
    expanding the plurality of micrografts; and
    applying the expanded plurality of micrografts to a patient recipient site.

11. The method according to claim 10, wherein the patient recipient site is an area of depigmented skin that has been prepared to receive the skin graft.

12. A method for generating and transferring micrografts, the method comprising:
providing a device comprising a base member, a micrograft generating station integrated with the base member; and a micrograft transferring station integrated with the base member;
obtaining a cartridge comprising a frame having a hollow inner portion, a removable first plate comprising a mesh grid, and a removable second plate comprising a mesh grid;
inserting a skin graft into the cartridge;
inserting the cartridge into the device;
engaging the micrograft generating station, thereby generating a plurality of micrografts; and
engaging the micrograft transferring station, thereby transferring the plurality of micrografts to a substrate.

13. The method according to claim 12, wherein
the cartridge in an assembled configuration, the mesh grid of the first removable plate and the mesh grid of the second removable plate are aligned with the hollow inner portion of the frame, and the mesh grid of the first removable plate is aligned with the mesh grid of the second removable plate; and
inserting the skin graft between the first and second removable plates such that the graft is aligned with the mesh grids in the first and second removable plates.

14. The method according to claim 13, wherein engaging the micrograft generating station comprises:
inserting the cartridge into the micrograft generating station while a frame of the device is in an open configuration; and
transforming the frame of the device from the open configuration to a closed configuration, thereby generating the plurality of micrografts.

15. The method according to claim 13, wherein engaging the micrograft transferring station comprises:
inserting the cartridge into the micrograft transferring station while a frame of the device is in an open configuration;
inserting a substrate below the cartridge; and
transforming the frame of the device from the open configuration to a closed configuration, thereby transferring the plurality of micrografts to the substrate.

16. The method according to claim 12, further comprising prior to the providing step: harvesting the skin graft.

17. The method according to claim 16, wherein harvesting comprises:
raising a blister; and
cutting the blister to obtain the skin graft.

18. The method according to claim 17, wherein said step of raising a blister comprises:
contacting a harvesting device having a hole to skin; and
applying heat and/or vacuum pressure, thereby raising the blister.

19. The method according to claim 12, further comprising:
expanding the plurality of micrografts; and
applying the expanded plurality of micrografts to a patient recipient site.

20. The method according to claim 19, wherein the patient recipient site is an area of depigmented skin that has been prepared to receive the skin graft.

* * * * *